(12) United States Patent
Hariyama et al.

(10) Patent No.: US 7,898,652 B2
(45) Date of Patent: Mar. 1, 2011

(54) METHOD AND APPARATUS FOR DETECTING DEFECTS ON A DISK SURFACE

(75) Inventors: Tatsuo Hariyama, Fujisawa (JP);
Hideaki Sasazawa, Yokohama (JP);
Minoru Yoshida, Yokohama (JP);
Shigeru Serikawa, Chigasaki (JP)

(73) Assignee: Hitachi High-Technologies Corporation, Tokyo (JP)

( * ) Notice: Subject to any disclaimer, the term of this patent is extended or adjusted under 35 U.S.C. 154(b) by 62 days.

(21) Appl. No.: 12/359,388

(22) Filed: Jan. 26, 2009

(65) Prior Publication Data
US 2009/0190123 A1    Jul. 30, 2009

(30) Foreign Application Priority Data
Jan. 30, 2008    (JP) .............................. 2008-019133

(51) Int. Cl.
*G01N 21/00*    (2006.01)
(52) U.S. Cl. ................. 356/237.2; 356/237.1; 356/445; 356/239.8; 356/442
(58) Field of Classification Search ... 356/237.1–237.6, 356/445, 442, 239.7, 239.8, 239.3
See application file for complete search history.

(56) References Cited

U.S. PATENT DOCUMENTS 7,656,171 B2 *    2/2010    Honda et al. ................. 324/751
2009/0237669 A1 *    9/2009    Hariyama et al. ............ 356/445

FOREIGN PATENT DOCUMENTS

| JP | 2000-180376 | 6/2000 |
| JP | 2001-066263 | 3/2001 |
| JP | 3732980 | 10/2005 |

* cited by examiner

*Primary Examiner*—Gregory J Toatley
*Assistant Examiner*—Iyabo S Alli
(74) *Attorney, Agent, or Firm*—Antonelli, Terry, Stout & Kraus, LLP.

(57) ABSTRACT

The present invention relates to an apparatus for detecting defects on a disk surface which projects light on the disk surface by a light transmitting system, receives specula reflection light and scattered light by a light receiving system, exposes defects by performing a two-dimensional frequency filter process on a signal, and performs a defect determination process to extract a linear-shaped isolative defect candidate. Next, the present invention performs a periodicity determination process to classify and detect the periodically generated linear and circular arc defects and the isolatively generated linear and circular arc defects.

20 Claims, 11 Drawing Sheets

FIG.8A    FIG.8B
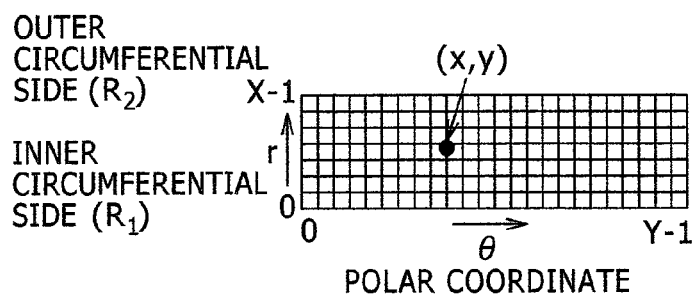
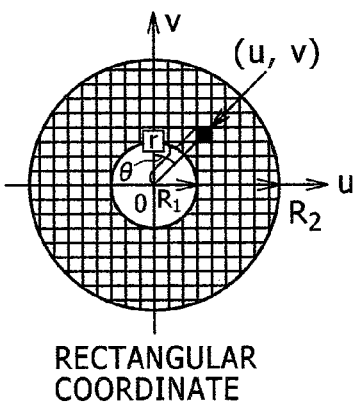
POLAR COORDINATE
RECTANGULAR COORDINATE
FIG.8C
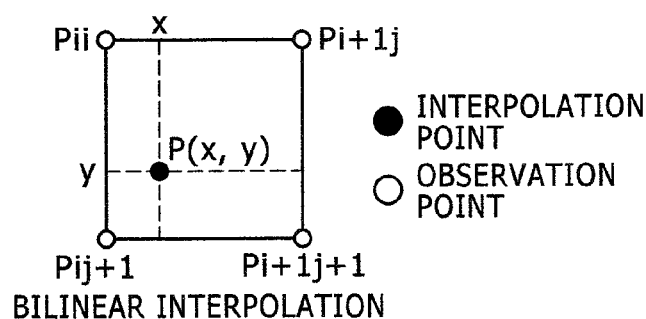
● INTERPOLATION POINT
○ OBSERVATION POINT
BILINEAR INTERPOLATION
FIG.9A    FIG.9B
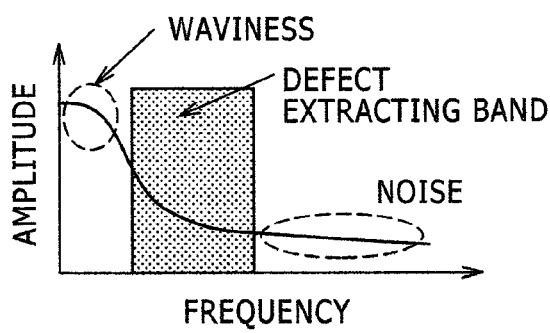
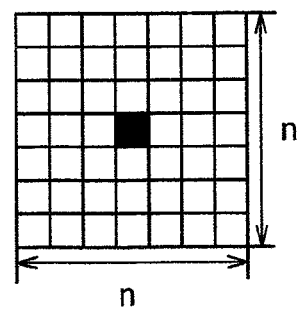

FIG.18A  FIG.18B
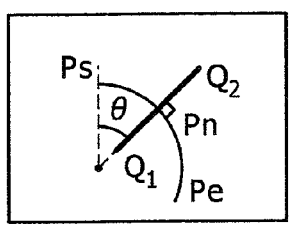 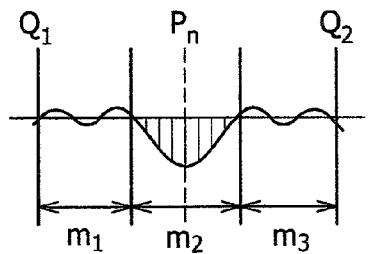
FIG.18C
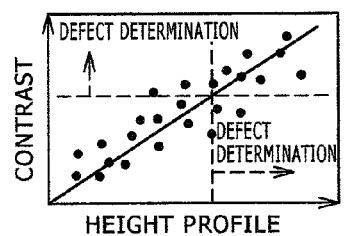
FIG.18D  FIG.18E
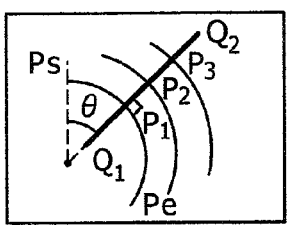 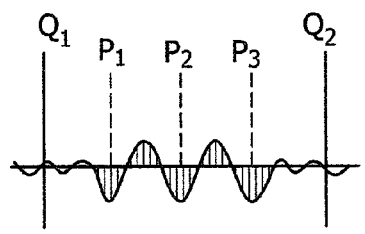
FIG.19A  FIG.19B
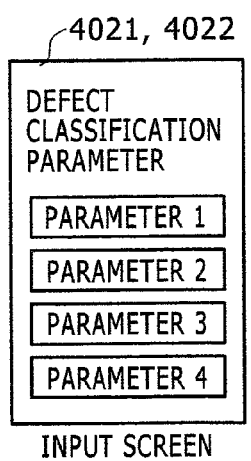 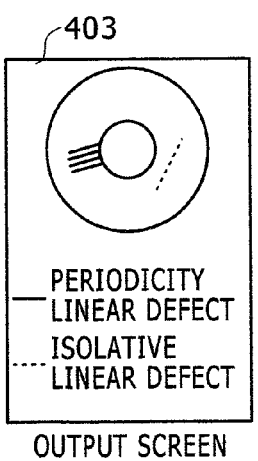 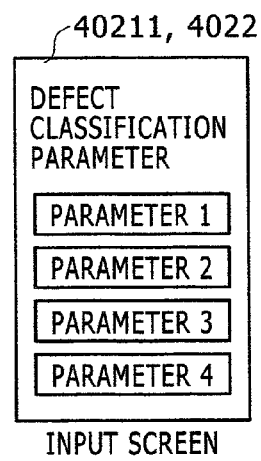 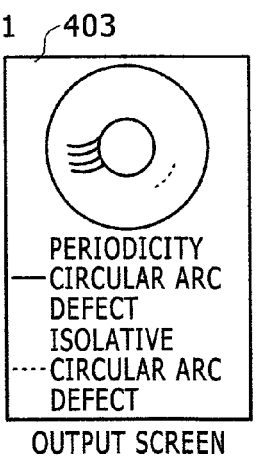

METHOD AND APPARATUS FOR DETECTING DEFECTS ON A DISK SURFACE

BACKGROUND OF THE INVENTION

1. Field of the Invention

The present invention relates to detect defects on a disk surface, and more particularly, to a method and apparatus for detecting linear defects and circular arc defects that exist on a disk surface and periodically occur.

2. Description of the Related Art

As a material of an information recording medium or a semiconductor, a disk such as glass, silicon wafer, and the like is used. When there are defects on the surfaces of these materials, characteristics of a product are deteriorated. As a result, detection of these defects is performed by an apparatus for detecting defects on a disk surface. The apparatus for detecting defects on the disk surface detects the defects generated on the disk surface. There are various kinds of defects, for example, fine dust (particle) attached to the surface, spot (stain), abrasion mark (scratch) due to foreign materials, fine concave portions (pit) or convex portions (bump), smoothly inclined concave portions (dimple), change (handling damage) of a disk edge caused due to collision, etc., at the time of delivering a disk, a grinding mark (glide) of a disk surface, and the like. As a method for effectively detecting these various defects, an apparatus for detecting defects on a disk surface according to the related art uses a method that detects defects by irradiating a laser beam on the disk surface and receiving each optical characteristic differently detected in terms of shape, size and the like of each defect, that is, reflected light or scattered light of the laser beam. FIG. 20 shows a schematic configuration of the apparatus for detecting defects on a disk surface that is disclosed in JP-A-2000-180376 and JP Patent No. 3732980 using the above-mentioned detecting method.

In addition to the above-mentioned defects, a defect called 'wrinkle shape' (hereinafter, referred to as wrinkle defect) is formed on the disk surface. The wrinkle defect is a defect that occurs during a process when the disk is shrunk by heat while the disk is manufactured. FIGS. 2A to 2E show features of the shape. FIG. 2A shows the whole disk and FIGS. 2B and 2C each show enlarged parts α and β where the wrinkle defect occurs. Further, FIG. 2D shows a cross sectional profile of FIG. 2B, and FIG. 2E shows a cross sectional profile of FIG. 2C. The wrinkle defect, which is a defect that periodically generates rugged portions in a linear shape or a circular arc shape, is a low aspect defect of which a height is very low as compared to the occurrence period of the defects. If the above defect exists on the disk surface, it makes a floating amount of a head unstable and affects the accuracy of magnetic reading and writing operations. As a result, this defect is considered as a serious defect. Therefore, a disk having the wrinkle on its surface is considered as a defective disk and may be thus treated like defective goods.

The apparatus (FIG. 20) for detecting defects on a disk surface known from the related art performs the detection for a low aspect (surface ruggedness) defect by allowing a light receiving element 202 to receive specula reflection light from a second light transmitting system 201. FIG. 3 illustrates the principle of detecting the low aspect defect. The second light transmitting system 201 has a configuration to project a parallel light having a predetermined width on a surface of the disk 301 that can detect the defects, and the light receiving element 202 has a configuration to receive the specula reflection light through a filter 203 (FIG. 3A). When a concave defect 3011 exists on the surface of the disk 301 (FIG. 3B), characteristics of the concave defect are similar to those of a concave lens, such that parallel light can be collected in the light receiving element 202. At this time, since a signal level detected by the light receiving element 202 is amplified, as shown in FIG. 3D as the amount of light received is amplified, it is possible to detect the concave defect by, for example, a threshold 2023. Further, when a convex detect 3012 exists on the surface of the disk 301 (FIG. 3C), the convex defect is operated like a convex lens, such that parallel light can be diffused and collected in the light receiving element 202. At this time, since the signal level detected by the light receiving element 202 is reduced and amplified, as shown in FIG. 3E as the amount of light received is reduced, it is possible to detect the convex defect by, for example, a threshold 2024.

However, since the increase and decrease of the signal are extremely small in the wrinkle defect portion, it is difficult to detect the wrinkle defect having extremely low aspect ratio among the low aspect defects. When detecting the wrinkle defects using an apparatus for detecting defects on a disk surface according to the related art, there are two problems as follows. The first problem is that the apparatus for detecting defects on a disk surface according to the related art detects the disk in a spiral shape as shown in FIG. 4 and performs a threshold process using a one-dimensional signal as a signal process. In this process, when the defects periodically exist in a radial direction (r direction) like the defect A of FIG. 4A, if the defect is detected in the spiral shape, a periodic change in a signal like a signal of FIG. 4B, which is intersected in a width direction of the defect, is obtained. However, if the signal strength is extremely small, when the threshold process is performed on the signal, the signal change can be hidden in the defect portion A by the change in the signal strength due to the waviness of the disk.

In order to avoid this, a band pass filter, which passes through only a frequency band in which the defects exist, is generally applied to the signal, making it possible to remove the waviness and detect the defects caused during the threshold process. However, when the defects periodically exist in a circumferential direction (θ direction) like the defect B of FIG. 4A, if the defects are detected in the spiral shape, there is a case where the change in the signal in the defect portion B like a signal of FIG. 4B that is intersected in a length direction of the defect is changed to be approximately the same as the period of the waviness. In this case, it is difficult to detect the defects even by using the filter process.

The second problem is that even if there is the signal strength signal in the wrinkle defect portion like the defect portion A, since the change in the signal strength is extremely small, the defects may be overlooked due to the setting of the threshold or a large amount of false reports may be generated. Further, distinguishing between the kinds of defects having linear or circular arc features, even if they are detected, are insufficient.

There is a problem of having a bad effect on a hard disk or a problem of generating a large amount of false reports by overlooking the wrinkle defect such that it is very inconvenient as the apparatus for detecting defects on a disk surface.

SUMMARY OF THE INVENTION

The present invention provides an apparatus for detecting defects on a disk surface that can accurately distinguish and detect defects without overlooking the wrinkle defects.

In other words, there is provided a method for detecting defects on a disk surface of the present invention including: irradiating light on the disk surface; detecting linear defects from light reflected on the disk surface; determining periodicity on the detected linear defects; and classifying and detecting the isolatively generated linear defects and the periodically generated linear defects based on the determination result of the periodicity.

Further, there is provided a method for detecting defects on a disk surface of the present invention including: irradiating light on the disk surface; detecting circular arc defects from light reflected from the disk surface; determining periodicity on the detected circular arc defects; and classifying and detecting the isolatively generated circular arc defects and the periodically generated circular arc defects based on the determination result of the periodicity.

Moreover, there is provided an apparatus for detecting defects on a disk surface of the present invention including: a projecting unit that irradiates a laser beam on the disk surface to scan the disk surface; a light receiving unit that receives reflection light of the laser beam due to defects existing on the disk surface; and a signal processing unit that detects defects from an output of the light receiving unit to perform determination for each kind of defect, wherein the signal processing unit detects linear defects from the output of the light receiving unit, determines periodicity on the detected linear defects, and classifies and detects the generated linear defects and the periodically generated linear defects based on the determination result of the periodicity.

In addition, the signal processing unit detects circular arc defects from the output of the light receiving unit, determines periodicity on the detected circular arc defects, and classifies and detects the generated circular arc defects and the periodically generated circular arc defects based on the determination result of the periodicity.

According to the present invention, the wrinkle defect, which is a low aspect defect, can be detected while suppressing false reports but not overlook the defects regardless of the generation direction of the wrinkle defect. Therefore, the present invention is advantage in that the quality of the detected disk is secured and in some cases, the yield of the disk product can be increased, and the production efficiency of the disk can be increased.

These and other objects, features and advantages of the invention will be apparent from the following more particular description of preferred embodiments of the invention, as illustrated in the accompanying drawings.

BRIEF DESCRIPTION OF THE DRAWINGS

FIG. 8A is a polar coordinate image that indicates a θ direction pixel on a horizontal axis and an r direction pixel on a vertical axis in an image obtained by a continuous signal detected;

FIG. 8B is a rectangular coordinate image that transforms the polar coordinate image of FIG. 8A from the polar coordinate image in an actual space so as to obtain a disk-shaped image and an actual defect-shaped image;

FIG. 8C is a diagram for explaining a bilinear interpolation that corrects a mismatch of the polar coordinate pixels corresponding to the rectangular coordinate pixels;

FIG. 9A is a diagram showing a band pass filter that passes through only a frequency band in which the wrinkle defects exist;

FIG. 9B shows an n×n digital filter as an example of the band pass filter;

FIG. 18A is a diagram showing the circular arc defects determined as isolative defects;

FIG. 18B is a diagram showing a distribution of the concentration value from a point $Q_1$ to a point $Q_2$ of the search region for each point from a starting point $P_s$ to an ending point $P_e$ of the circular arc;

FIG. 18C is a diagram showing a relationship between a defect contrast value of the circular arc defects determined as the isolative defects and a height measuring value due to an actual profile;

FIG. 18D is a diagram showing a state that sets the search regions $Q_1$ to $Q_2$ for each point from a starting point to an ending point of the line segment in a drawing for explaining a method that obtains a height of the circular arc defect determined as periodicity defects;

FIG. 18E is a diagram showing a distribution of the concentration value from a point $Q_1$ to a point $Q_2$ in the search region;

FIG. 19A is a diagram showing a screen that inputs a linear defect classification parameter and a screen that outputs a linear defect detection result;

FIG. 19B is a diagram showing a screen that inputs a circular arc defect classification parameter and a screen that outputs a circular arc defect detection result.

DESCRIPTION OF THE PREFERRED EMBODIMENTS

Hereinafter, embodiments will be described with reference to the accompanying drawings.

First Embodiment

Figure 1:
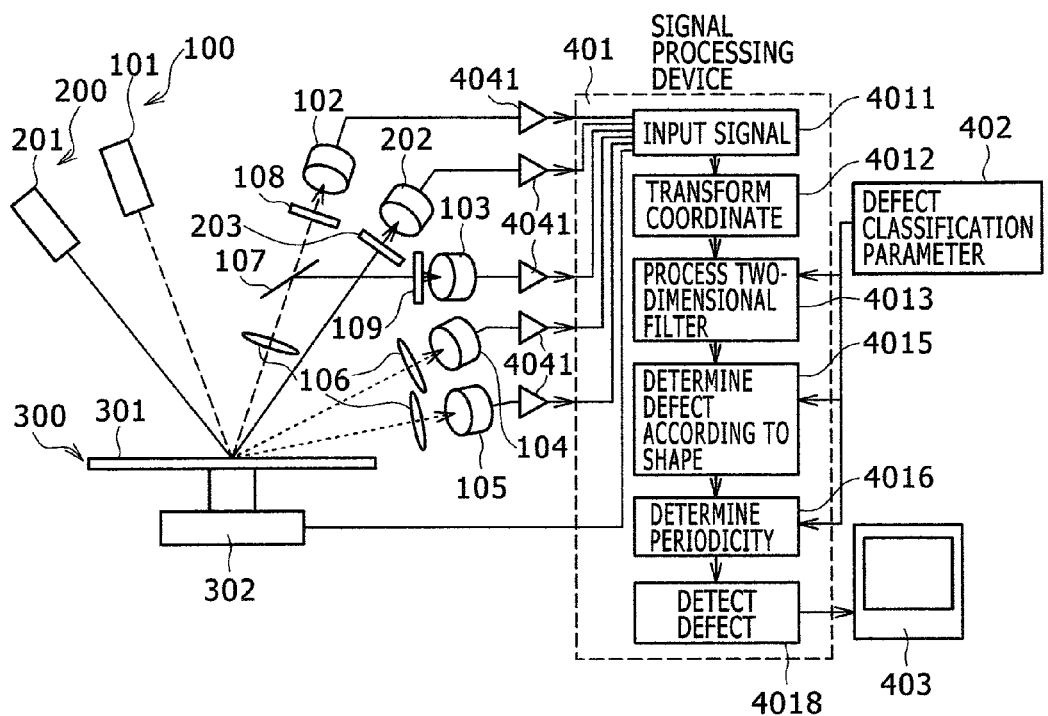
FIG. 1 is a diagram showing a schematic configuration of an apparatus for detecting defects on a disk surface.
Figure 2A:
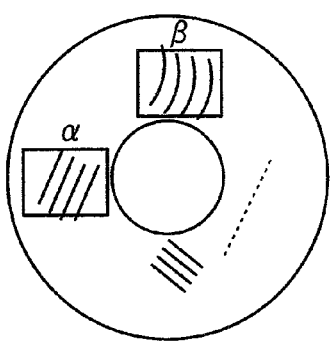
FIG. 2A is a diagram showing an entire surface of the disk.
Figure 2B:
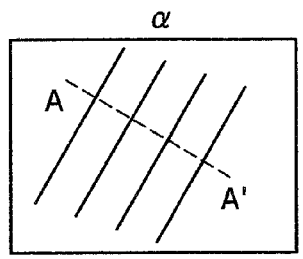
FIG. 2B is an enlarged diagram of the wrinkle defect α shown in FIG. 2A.
Figure 2C:
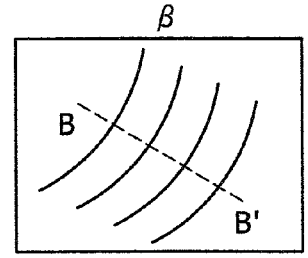
FIG. 2C is an enlarged diagram of the wrinkle defect β shown in FIG. 2A.
Figure 2D:
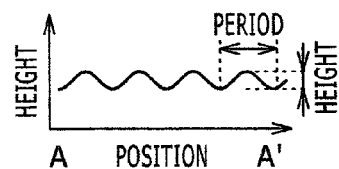
FIG. 2D is a diagram showing a cross section profile of the disk at places where the wrinkle defect α shown in FIG. 2B occurs.
Figure 2E:
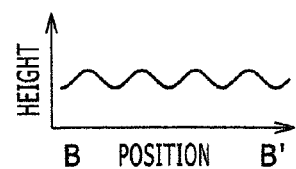
FIG. 2E is a diagram showing a cross section profile of the disk at places where the wrinkle defect β shown in FIG. 2C occurs.
Figure 3A:
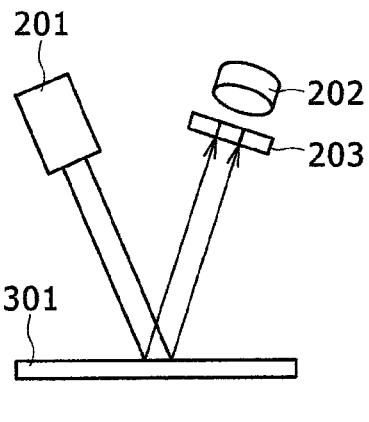
FIG. 3A is a configuration to allow a light transmitting system to project parallel light having a predetermined width on a disk surface that can detect defects and the light receiving element to receive the specula reflection light through a filter.
Figure 3B:
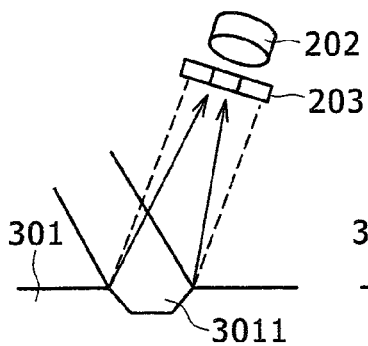
FIG. 3B is a configuration to project parallel light having a predetermined width on the disk surface to allow the light receiving element to receive the specula reflection light through a filter when concave defects exist on the disk surface.
Figure 3C:
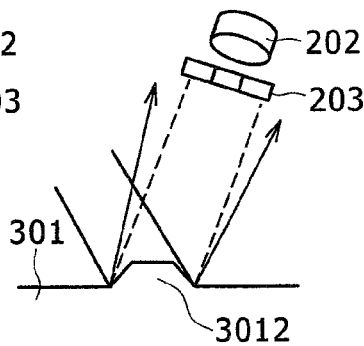
FIG. 3C is a configuration to project parallel light having a predetermined width on the disk surface to allow the light receiving element to receive the specula reflection light through a filter when convex defects exist on the disk surface.
Figure 3D:
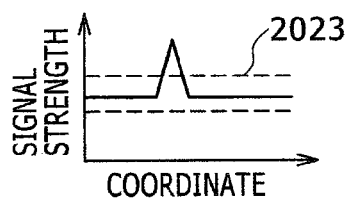
FIG. 3D is a diagram showing a signal level that is detected by the light receiving element when the concave defects exist on the disk surface shown in FIG. 3B.
Figure 3E:
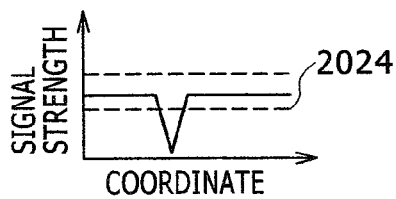
FIG. 3E is a diagram showing a signal level that is detected by the light receiving element when the convex defects exist on the disk surface shown in FIG. 3C.

FIG. 1 is a diagram schematically showing an entire configuration of an apparatus for detecting defects on a disk surface according to a first embodiment. As shown in FIG. 1, the apparatus for detecting defects on a disk surface includes dual optical systems 100 and 200 that are each configured with a light transmitting system and a light receiving system. For example, the first optical system 100 detects pit, handling damage, stain, particle, and scratch defects and the second optical system 200 detects bump, dimple, and glide defects. In other words, the plural optical systems are disposed according to the kind of defect. The first light transmitting system 101 projects light to form laser spots on a surface of a disk 301, and the second light transmitting system 201 projects parallel light having a predetermined width, which can detect defects, on the surface of the disk 301 and at the same time, scans the position thereof on the surface of the disk 301 in a spiral shape at a stage 302. When the defects exist on the surface of the disk 301, the laser spot is scattered, and therefore the plural defect data signals are obtained by allowing each light receiving system to receive the scattered light.

In other words, the first light receiving element 102 receives a bright view field portion of the scattered light from the first light transmitting system 101 (that is, laser spot), and second light receiving elements 104 and 105 receive a dark field portion of the scattered light (however, in this example, the light receiving element 105 receives the dark field portion scattered in a low angle direction from the disk surface, and the light receiving element 104 receives the dark field portion scattered in a high angle direction). The light receiving element 103 receives specula reflection light from the first light transmitting system 101, and a light receiving element 202 receives the specula reflection light from the second light transmitting system 201, respectively. When there are defects, the specula reflection light increases and decreases and is then received in each of the light receiving elements 103 and 104. Thus, each of the light receiving elements is disposed so that it corresponds to the specula reflection light or the scattered light having different light strength according to the kind of defects. In addition, in order to receive targeted light (that is, the specula reflection light or the scattered light) with high efficiency, elements such as filters 108, 109, and 203, a lens 106, and the like are disposed.

Light received by each of the light receiving elements is transformed into each defect data signal through an amplifier circuit 4041 and the like, which is in turn input to a signal processing device 401 (4011). Next, the defect data signal is subjected to a coordinate transformation process from a polar coordinate to a rectangular coordinate and is stored in an address of a memory corresponding to a predetermined unit cell (for example, a micro rectangular cell that is formed as a micro distance Δr in a radial direction and a micro distance Δθ in a circumferential direction on the disk) on the disk surface (4012). Thereafter, a filter process is performed on a coordinate transformed image (4013). Further, the defect determination is performed from a shape feature of the defect such as the continuity and density of the stored address and the like (4015), and determination on periodicity for a line segment determined as the linear defect or the circular arc defect in the defect determination is performed (4016). What is detected as the defect (4018) is output from an output device 403.

The apparatus for detecting defects on a disk surface is configured of the optical system 100 and the optical system 200 that includes the light transmitting system and the light receiving system, respectively and is disposed at a predetermined position so that the light transmitting system and the light receiving system can detect plural defects on the surface of the disk 301. In the first embodiment, each of the "pit", "handling damage", "stain", "particle", and "scratch" defects is detected by the first optical system 100, and each of the "bump", "dimple", and "glide" defects is detected by the second optical system 200. The wrinkle defect is detected by the second optical system 200.

Figure 6:
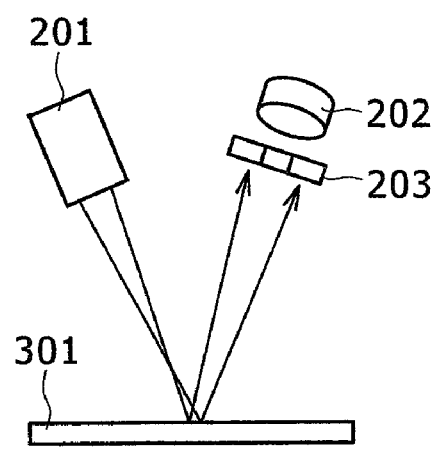
FIG. 6 is a diagram showing another configuration example of the light transmitting system of the apparatus for detecting defects on a disk surface.

The detection of the wrinkle defect is performed by allowing the light receiving element 202 to receive the specula reflection light from the second light transmitting system 201. The result obtained by performing the detection on the wrinkle defect shown in FIGS. 2A to 2E uses the optical system shown in FIGS. 5A to 5D. Comparing FIGS. 2A to 2E with FIGS. 5A to 5D, the ruggedness of the height and the ruggedness of the signal strength are inverted to each other. This is because a concave defect increases signal strength and a convex defect decreases in signal strength, as shown in the detection principle of FIGS. 3A to 3E. However, the features, which periodically generate the linear defect or the circular arc defect, do not change. Moreover, although the detection principle using the parallel light as the light transmitting system 201 in FIGS. 3A to 3E with regard to the optical system 200 is described, it is possible to detect the concave and convex defects on the surface by using converged light shown in FIG. 6 as the light transmitting system similarly to the above detection principle using the parallel light.

Figure 7:
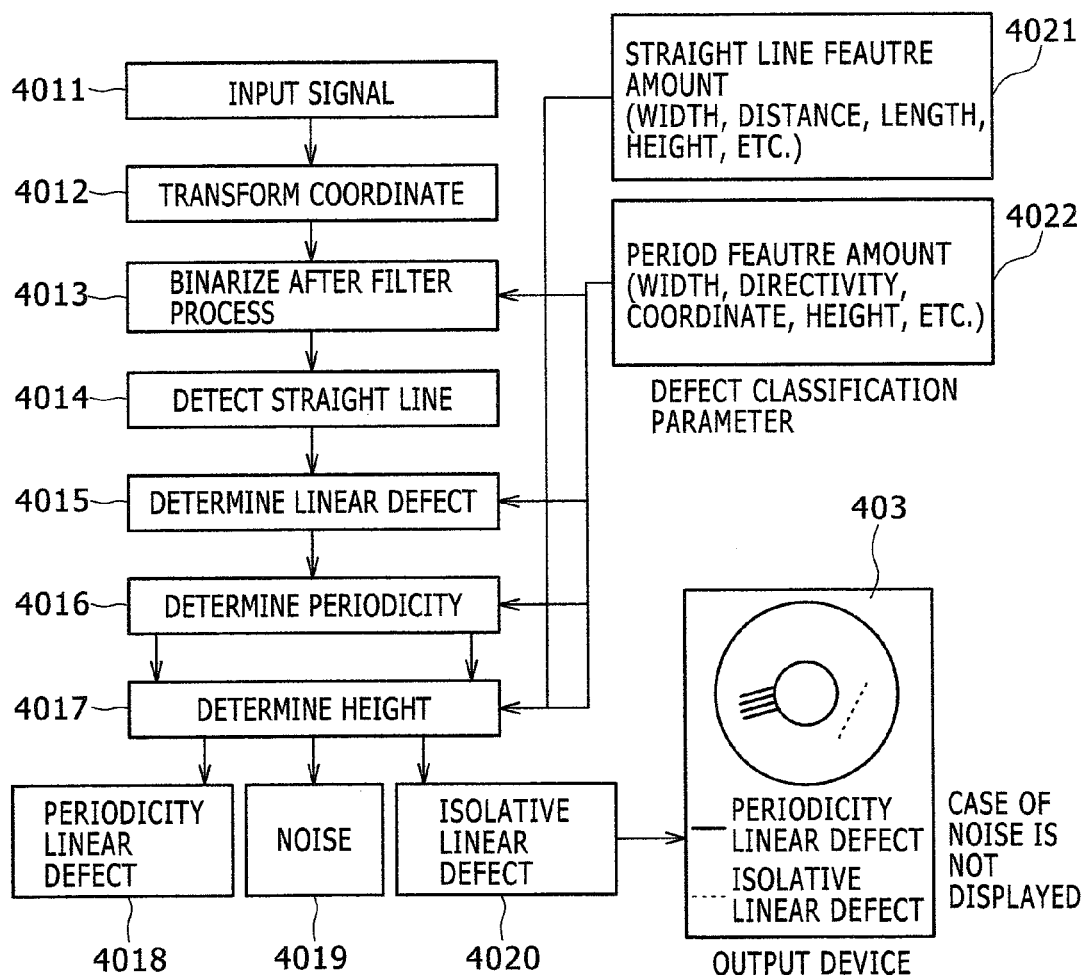
FIG. 7 is a flow chart showing a process that detects linear defects having periodicity in a first embodiment.

FIG. 7 is a flow chart showing one example of a program that performs the determination on the kind of defects executed in the signal processing device 401 of FIG. 1. The processing flow chart is a flow chart that performs determination on the wrinkle defect that occurs in a linear shape. The flow chart determining the wrinkle defect that occurs in the circular arc shape will be described later. The process starts by inputting the defect data signal from the light receiving element 202 that detects the wrinkle defect, that is, allowing the light receiving element 202 at a hardware side (that is, an optical system side) to receive the signal strength change that is generated by the wrinkle defect (4011).

Figure 4A:
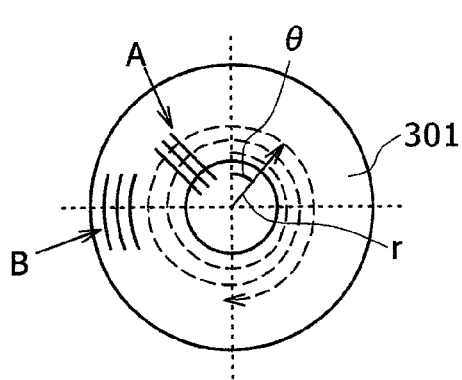
FIG. 4A is a diagram showing a state where there are a periodic defect A in a radial direction (r direction) on the disk surface and a periodic defect B in a circumferential direction (θ direction)
Figure 4B:
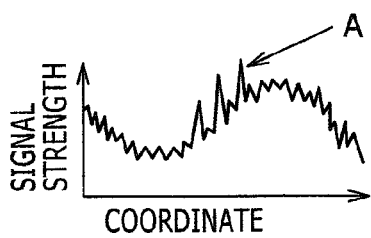
FIG. 4B is a diagram showing a signal obtained by detecting the defect A on the rotating disk surface.
Figure 4C:
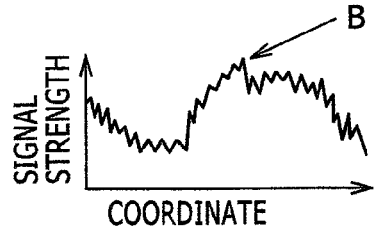
FIG. 4C is a diagram showing a signal obtained by detecting the defect B on the rotating disk surface.
Figure 5A:
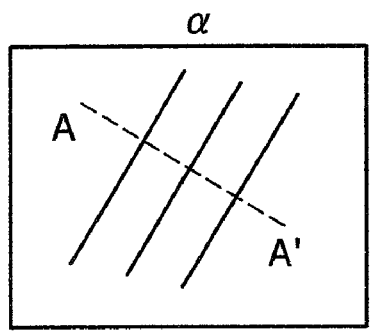
FIG. 5A is an enlarged diagram showing the wrinkle defects α shown in FIG. 2A.
Figure 5B:
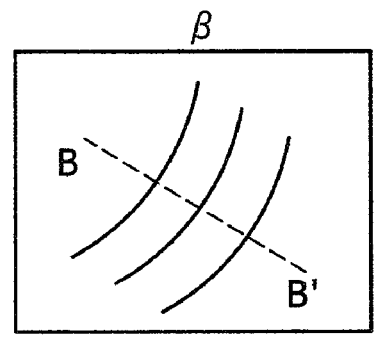
FIG. 5B is an enlarged diagram showing the wrinkle defects β shown in FIG. 2A.
Figure 5C:
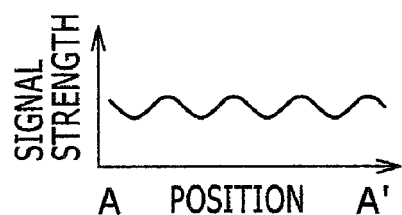
FIG. 5C is an enlarged diagram showing the wrinkle defects α shown in FIG. 2A.
Figure 5D:
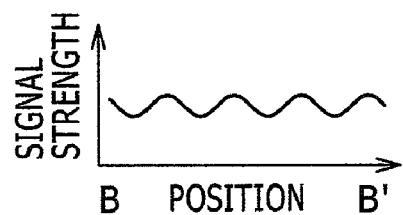
FIG. 5D is an enlarged diagram showing the wrinkle defects β shown in FIG. 2A.

When a signal through a circuit (an amplifier 4041, and the like) from the light receiving element 202 at a software side (that is, a signal processing device 401 side) is input (4011), the coordinate transformation process from the polar coordinate to the rectangular coordinate is performed (4012). FIGS. 8A to 8C show the coordinate transformation process of the acquisition signal. Since the detection apparatus uses a spiral scanning method as shown in FIGS. 4A to 4C, the image acquired by the detected continuous signal becomes the polar coordinate image that takes a θ direction pixel at a horizontal axis and an r direction pixel at a vertical axis as shown in FIG. 8A. In order to obtain the disk shape image and the actual defect shape image in the actual space from the polar coordinate image, it needs the coordinate the transformation from the polar coordinate to the rectangular coordinate (FIG. 8B). The transformation from the pixels (x and y) among the polar coordinate images to the pixels (u and v) among the rectangular coordinate images uses the following equation.

$$u = \left\{\frac{R_2 - R_1}{X}(x) + R_1\right\}\sin\left(2\pi\frac{y}{Y}\right)$$
$$v = \left\{\frac{R_2 - R_1}{X}(x) + R_1\right\}\cos\left(2\pi\frac{y}{Y}\right)$$ [Equation 1]

wherein $R_1$ indicates an inner circumferential radius of the disk, $R_2$ indicates an outer circumferential radius of the disk, and X and Y indicate the number of the r direction pixels and the number of the θ direction pixels of the polar coordinate image, respectively. Herein, since each pixel (observation point) has a discrete value, the polar coordinate pixel (x and y) corresponding to the rectangular coordinate pixel (u and v) do not match agree with the observation point. The mismatch is corrected by the bilinear interpolation at the adjacent observation point. The bilinear interpolation performs the interpolation by the following equation using image data of four observation points around an interpolation point as shown in FIG. 8C.

$$P_{(xy)} = \{(i+1)-x\}\{(j+1)-y\}P_{ij} + \{(i+1)-x\}\{y-j\}P_{ij+1} + \{x-i\}\{(j+1)-y\}P_{i+1j} + \{x-i\}\{y-j\}P_{i+1j+1}$$ [Equation 2]

wherein i and j are each the integer parts (observation points) of x and y.

Next, the filter process is performed on the coordinate transformed image (4013). Since the wrinkle defect is a low aspect defect and the signal strength is extremely small, when the threshold process is performed on the signal, there is the possibility of burying the signal change in the defect portion according to the signal strength change due to the waviness of the disk or the noise of the high frequency device. In order to avoid this, as shown in FIG. 9A, a band pass filter, which passes through only a frequency band in which the wrinkle defects exist, is applied to the signal, making it possible to remove the waviness and noise and detect the defects caused due to the threshold process. Herein, the frequency band is obtained from a period parameter of the defect that is set by a user (or previously set to the device). An example of the filter is shown in FIG. 9B. FIG. 9B show an n×n digital filter, wherein the filter process is performed on the image by convoluting the filter. The size and coefficient of the filter are determined so that the filter has a characteristic of passing through only the frequency band in which the wrinkle defects exist. Further, the binarization process on the image, which is subjected to the filter process, is compared with the threshold set by the user (or previously set to the device).

Figure 10A:
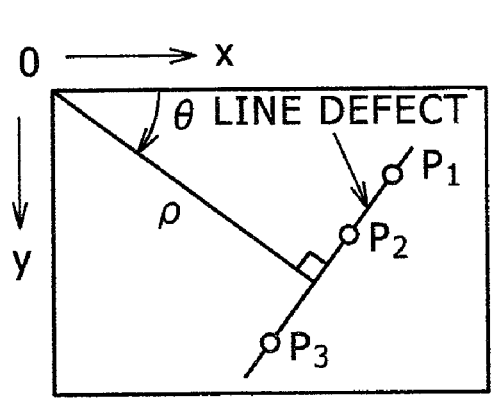
FIG. 10A is shows an image of an actual space (x and y) when extraction of a straight component of a binarized image is performed.
Figure 10B:
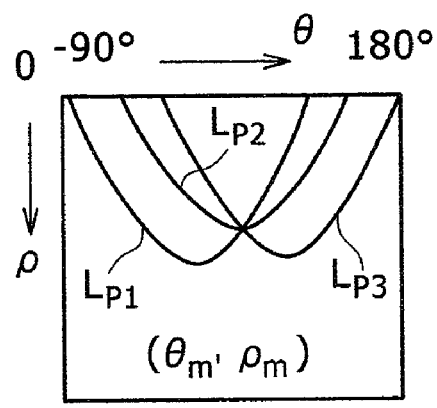
FIG. 10B is a diagram showing an image on a Hough space.

Next, the extraction of straight component of the image binarized by the process is performed (4014). As an example for performing the straight detection, a Hough transform method is used. FIGS. 10A and 10B show a principle of the Hough transformation. FIG. 10A shows an image on the actual space (x and y) and FIG. 10B shows the Hough space. For example, if three points, that is, $P_1$, $P_2$, and $P_3$ exist on a straight line, the equation of a straight line becomes the following equation.

$$\rho = i \times \cos\theta + y\sin\theta$$ [Equation 3]

wherein ρ is a perpendicular length lowered along a straight line from the left corner of the image and θ is an angle perpendicular to the x axis. At this time, one straight line is equivalent to one point on a θ–ρ parameter space shown in FIG. 10B. Each point ($P_1$, $P_2$, and $P_3$) having a value of 1 in a binary image, which becomes an object, computes a pair of (θ and ρ) satisfying the above equation and plots the point as $L_{p1}$ to $L_{p3}$ of the FIG. 10B. $L_{p1}$ to $L_{p3}$ are intersected at only one point ($\theta_m$ and $\rho_m$) and the point indicates a straight line formed by $P_1$, $P_2$, and $P_3$ of FIG. 10A. In other words, if a point (the points $\theta_m$ and $\rho_m$ of the greatest frequency) where the frequencies most commonly intersect are generated and selected on the θ–ρ parameter space, the straight line where the ($\theta_m$ and $\rho_m$) is determined is the most predominant straight component on the object image. The extraction of the straight component is performed based on the above principle.

Figure 11:
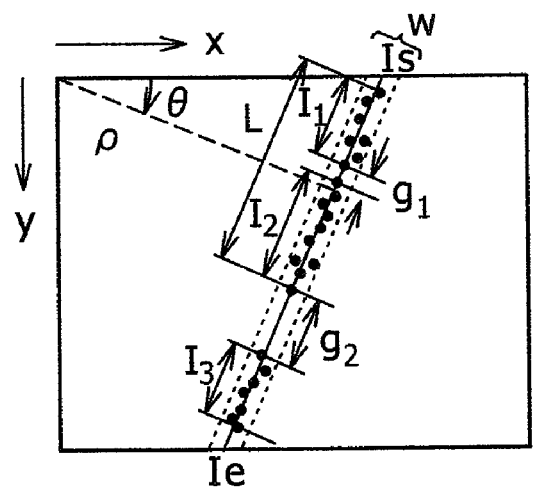
FIG. 11 is a diagram showing a length measuring result of the straight line detected by a Hough transformation.

Next, the linear defect determination is performed on the plural extracted line segments in respects to the distance between the composition points and the line segment length (4015). FIG. 11 shows the determination method. In FIG. 11, the straight line for the points selected on the θ-ρ parameter space is drawn on the x and y spaces, the threshold parameter W having a width set by the user (or previously set to the device) for the straight line is taken, and a group of points existing in the range becomes a group of points forming the straight line. The reason why the threshold parameter has the width is that the actual linear defect becomes a line segment having a predetermined width without being overlapped with one line. Next, a distance $g_i$ (i=1, 2 . . . ) between the group of points is obtained, and if the distance is smaller than the threshold parameter $g_t$ of the distance set by the user (or previously set to the device), the group of points is considered to be continuous and if it is larger than the threshold parameter $g_t$, it is considered to be separated. Next, the distance $l_i$ (i=1, 2 . . . ) (a line segment length) between points of both ends for the group of connected points is obtained, and if the distance is smaller than the threshold parameter $l_t$ of the length set by the user (or previously set to the device), it is considered that the group of points do not have defects and if distance is larger than the threshold parameter $l_t$, it is considered that the group of points has defects. As shown in detail in FIG. 11, if intervals $g_1$ and $g_2$ become $g_1 < g_t < g_2$, $l_1$ and $l_2$ become one line segment and $l_3$ becomes an independent line segment. Further, if the line L, $l_3$, and $l_t$ become $l_3 < l_t < L$, L is finally detected as a defect.

Figure 12A:
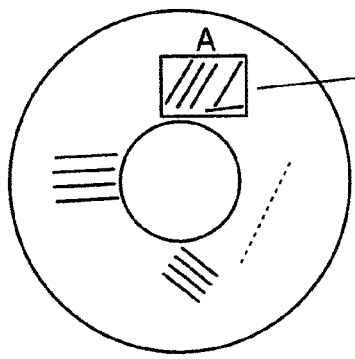
FIG. 12A is a diagram showing an image on the disk surface.
Figure 12B:
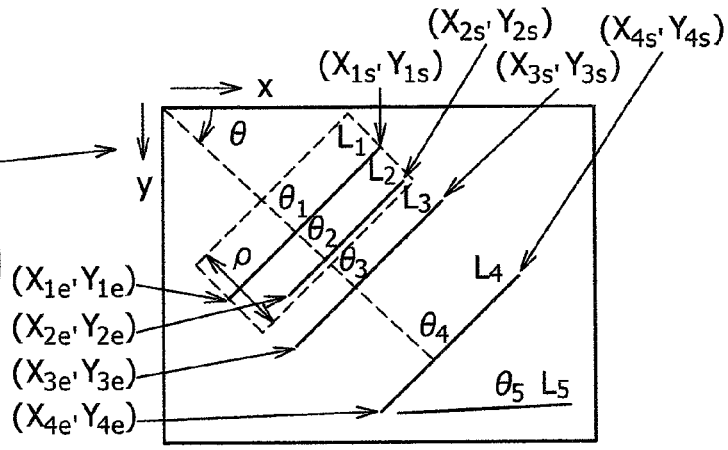
FIG. 12B is an enlarged diagram of a place A portion where several lines detected as a linear defect candidate exist in an image on the disk surface.

Next, the periodicity determination on the line segment determined as the linear defect is performed (4016). FIGS. 12A and 12B show the determination method. FIG. 12B is an enlarged diagram of a portion of place A where several line segments determined as a linear defect exist in an image on the disk of FIG. 12A. Herein, the determination process on periodicity is performed using the line segment L1 as a reference of the periodicity determination (4016). First, the directionality determination is performed by the directionality threshold parameter Δθ set by the user (or previously set to the device). In other words, with regard to an angle θ of a straight line obtained at the time of performing the Hough transformation, the line segment, which is within the range of $θ_1 ± Δθ$, is taken out as a candidate line segment having periodicity for the line segment $L_1$. For example, in the case of the FIG. 12B, it is determined that $θ_2, θ_3,$ and $θ_4$ are matched with each other in terms of directionality and $θ_5$ is not matched in terms of directionality. Next, a region surrounded in a square shape from a starting point coordinate ($x_{ls}$ and $y_{ls}$) of $L_1$, an ending point coordinate ($x_{le}$ and $y_{le}$), and the threshold parameter ρ of the period set by the user (or previously set to the device) is considered, and it is determined that there are the line segment L1 and the periodicity for the line segment, which is within the region. For example, in the case of FIG. 12B, the region is a region shown by a dotted line and it is determined that $L_2$ included in the region has periodicity. Likewise, if $L_2$ is considered as a reference, it is determined that $L_3$ has periodicity and finally, it is determined that $L_1, L_2$ and $L_3$ are a group of line segments having periodicity.

Figure 13A:
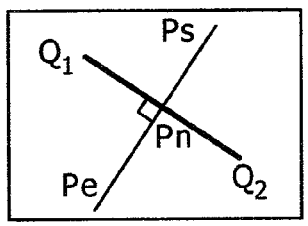
FIG. 13A is a diagram showing a state that sets search regions $Q_1$ to $Q_2$ orthogonal to lines, including each point from a starting point $P_s$ to an ending point $P_e$ of the line.
Figure 13B:
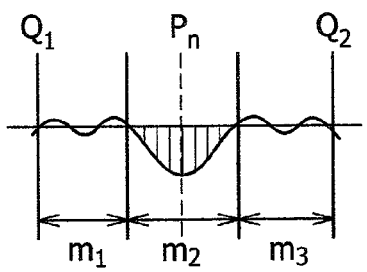
FIG. 13B is a diagram showing a concentration value from a point $Q_1$ to a point $Q_2$ in each search region by segmenting the search regions $Q_1$ to $Q_2$ into three regions of $m_1$, $m_2$, and $m_3$.

Determination on a height for the linear defect subjected to the periodicity determination is finally performed (4017). Since the ruggedness amount of the disk surface makes the floating amount of the head unstable, it is necessary to perform the defect determination depending on the height. FIGS. 13A to 13E show an example of performing the height determination from the image data. When a surface of a face plate is examined using the optical system shown in FIG. 3, since the height information appears as a contrast on the image, the height determination is performed using the contrast information. In the line segment determined as an isolative defect and the line segment having periodicity in the step of the periodicity determination, since a method for determining the height has a slight difference, the method that obtains the height for the line segment determined as the isolative defect will be first described referring to FIGS. 13A and 13B. With regard to each point from a starting point $P_s$ to an ending point $P_e$ of the line segment as shown in FIG. 13A, the search regions $Q_1$ to $Q_2$ orthogonal to the line segment including the points are set such that the contrast of the line segment is obtained from the concentration value from the point $Q_1$ to the point $Q_2$ in the search region. Describing this through FIG. 13B, it is considered that the search regions $Q_1$ to $Q_2$ is divided into $m_1, m_2,$ and $m_3$ and the line segment exists in the region $m_2$. Since the contrast is compared with a circumferential portion, an average concentration at the portion is computed by the following equation from portions $m_1$ and $m_3$ that are outside of the line segment.

$$C_n = \sum_{i \in D_2} \left| \left\{ \frac{1}{m_1 + m_3} \right\} \cdot \sum_{j \in D_1 + D_3} \{f_j\} - f_i \right|$$ [Equation 4]

A difference between the average concentration value and the concentration value of the region $m_2$ is obtained, and the concentration value obtained by integrating the difference in the region $m_2$ is obtained as the contrast at the point $P_n$ in the line segment.

If a $C_n$ value is computed from the starting point $P_s$ to the ending point $P_e$ of the line segment, subjected to the accumulation addition, and divided by the line segment length L, the average contrast $C_{av}$ is obtained.

$$C_{av} = \left( \sum_{P_s}^{P_e} C_n \right) / L$$ [Equation 5]

Figure 13C:
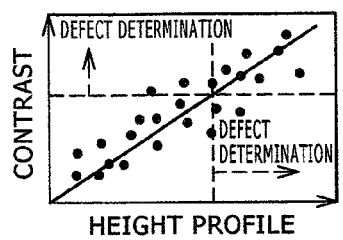
FIG. 13C is a diagram showing a relationship between a defect contrast value and a height measuring value due to an actual profile.

The defect determination can be performed from the contrast of the linear defect that is detected by making the correlation between the height measuring value according to the actual profile (measured by other devices) and the obtained contrast value into the shape as shown in FIG. 13C.

Figure 13D:
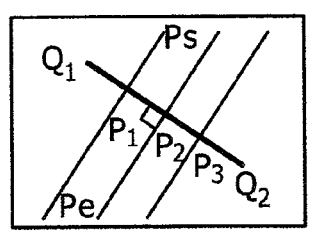
FIG. 13D is a diagram showing a state that sets the search regions $Q_1$ to $Q_2$ for each point from a starting point to an ending point of the line segment in a drawing for explaining a method that obtains a height of the line segment determined as periodicity defects.
Figure 13E:
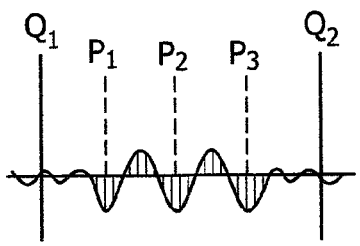
FIG. 13E is a diagram showing a distribution of the concentration value from a point $Q_1$ to a point $Q_2$ in the search region.

Next, the method for obtaining the height for the line segment determined as the periodicity defect will be described using FIGS. 13D and 13E. As shown in FIG. 13D, with regard to each point from the starting point $P_s$ to the ending point $P_e$ of the line segment, the search regions $Q_1$ to $Q_2$ orthogonal to the line segment including the points are set such that the contrast of the line segment is obtained from the concentration value from the point $Q_1$ to the point $Q_2$ in the search region. Describing this through FIG. 13E, since the surface ruggedness continuously occurs in the periodic defect, it is considered that the level difference of the concentration continuously occurs. The average concentration value of the search regions $Q_1$ to $Q_2$ is obtained, the absolute value of the difference between the average concentration value and the concentration value of the search regions $Q_1$ to $Q_2$ is obtained, the obtained absolute value of the difference is integrated in the search regions $Q_1$ to $Q_2$, and the value divided by the number of line segments included in the regions $Q_1$ to $Q_2$ is obtained as the contrast at the points $P_1$, $P_2$, and $P_3$ in the periodic line segment.

$$C_n = \sum_{i=Q_1}^{Q_2} \left| \sum_{j=Q_1}^{Q_2} \{f_j\} - f_i \right| \quad \text{[Equation 6]}$$

If the $C_n$ value is computed from the starting point $P_s$ to the ending point $P_e$ of the line segment, subjected to the accumulation addition, and divided by the line segment length L, the average contrast $C_{av}$ is obtained as follows.

$$C_{av} = \left( \sum_{P_s}^{P_e} C_n \right) / L \quad \text{[Equation 7]}$$

The defect determination can be performed on the basis of the contrast of the linear defect that is detected by making the correlation between the height measuring value according to the actual profile (measured by other devices) and the obtained contrast value into the shape as shown in FIG. 13C.

As shown in FIG. 7, periodicity linear defect detection (4018), isolative linear defect detection (4020), and noise detection (4019) are finally formed which are output from the output device 403 by the process. Further, the input of the defect classification parameters (4021) and (4022) is input by the user from the input screen of the defect classification parameter input device 402, for example, as shown in FIG. 19A, and the output of the detection result is displayed by, for example, separate colors for each kind of defect as displayed on the output screen 403.

Further, according to the first embodiment, the periodicity linear defect, which is the low aspect defect, can be detected while suppressing false reports and not overlooking the defects regardless of the generation direction of the periodicity linear defect.

Second Embodiment

Figure 14:
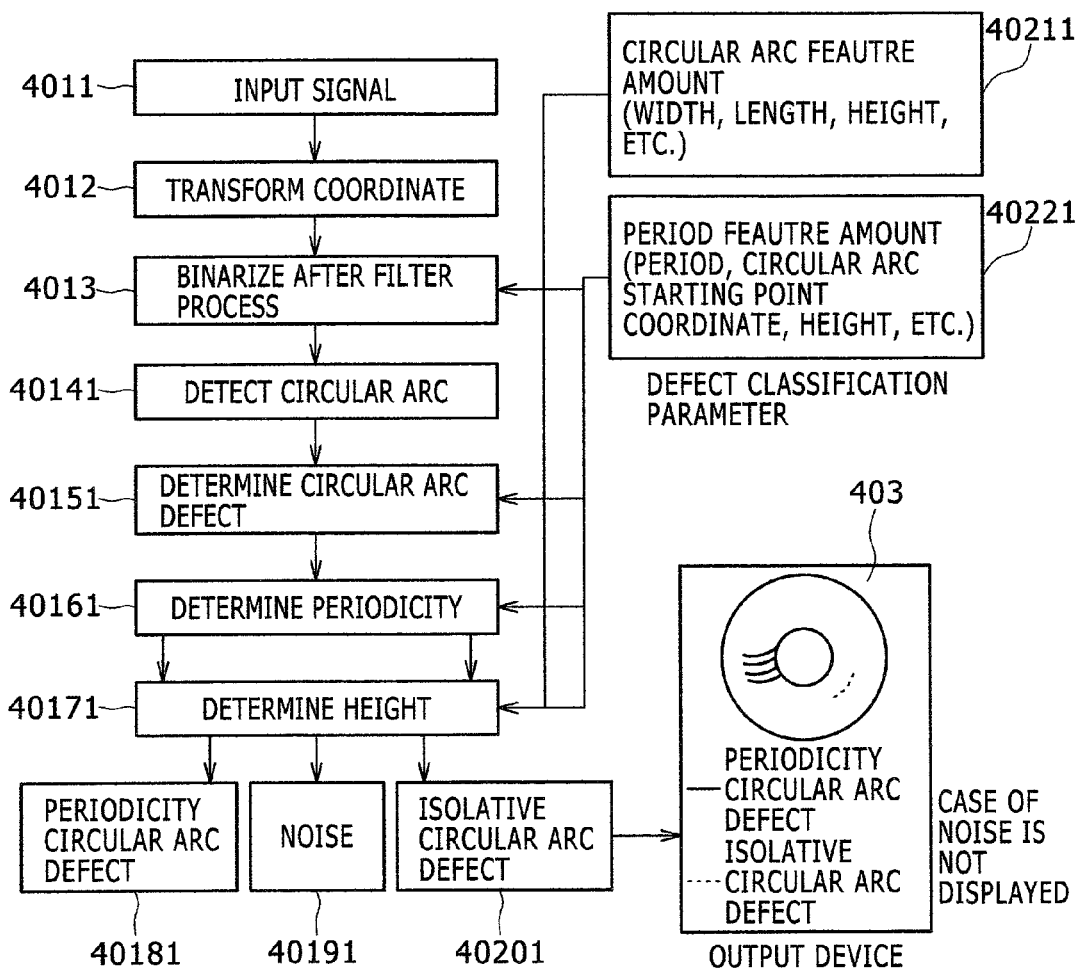
FIG. 14 is a flow chart showing a process that detects periodicity circular arc defects according to a second embodiment.

Next, the determination method of the wrinkle defect generated in the circular arc shape will be described as the second embodiment. FIG. 14 describes an image processing flow on the defect having the features of the circular arc distribution. The processing contents from 4011 to 4013 of FIG. 14 are the same as the process described in FIG. 7.

Figure 15A:
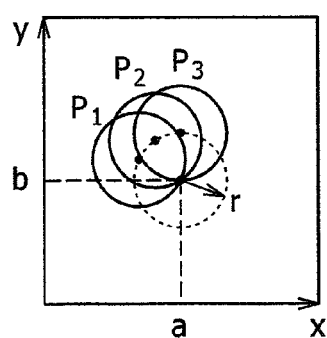
FIG. 15A is a diagram showing a case where three points have a circle with the same radius r in the drawing for explaining a principle of the circular arc detection by the Hough transformation.
Figure 15B:
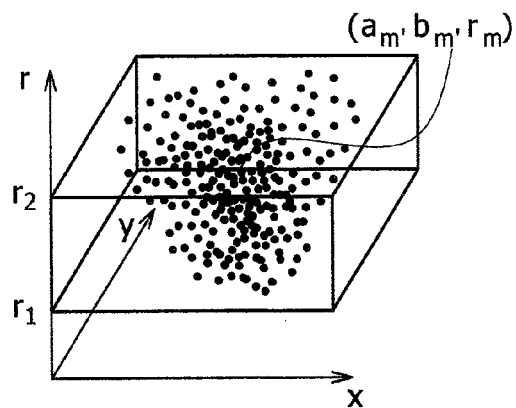
FIG. 15B is a diagram showing a state plotting information on the circular arc in a space that is made by a center coordinate (a and b) and a radius of a circular arc.

Next, the extraction of circular arc component of the image binarized by the process is performed (40141). As an example for performing the circular arc detection, the Hough transform method is used. FIGS. 15A and 15B show a principle of the Hough transformation. For example, in FIG. 15A, if three points, that is, $P_1$, $P_2$, and $P_3$ exist on the same circle having a radius r, the circle equation becomes the following equation.

$$(x-a)^2 + (y-b)^2 = r^2 \quad \text{[Equation 8]}$$

However, a and b become the center coordinate of a circle. The method for obtaining the center coordinate (a and b) indicates the circle having the radius r based on the points $P_1$, $P_2$, and $P_3$ and the point that most intersects the circle becomes the center coordinate (a and b). If the process is performed on '1' pixel for the entire image, the center coordinate candidates of the circle whose radius is r are enumerated. The radius of the circular arc defect, which may be the defect, is an arbitrary value, for example, the defect from the radius $r_1$ to $r_2$ becomes an object range of the radius that is the fatal defect. In this case, the vote that chooses the point that most intersects the circle is performed in the space ($a_m$, $b_m$, and $r_m$) to obtain the radius and center coordinates of the circular arc defect from the selected point.

Figure 16:
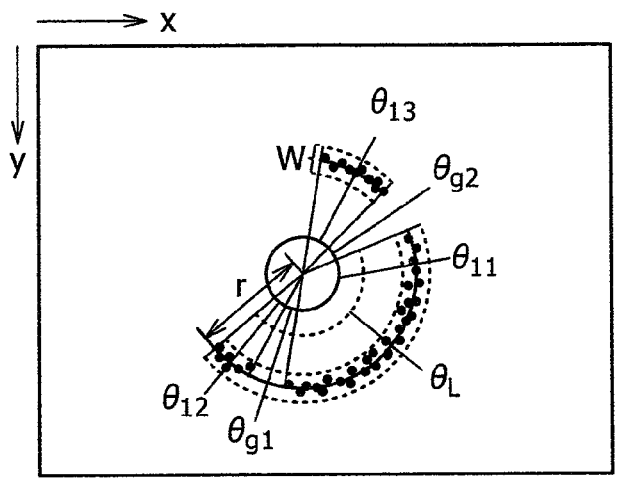
FIG. 16 is a diagram for explaining a method that performs the determination on the circular arc defects detected by the Hough transformation.

Next, the determination of the circular arc defect is performed on the plural extracted circular arcs by the distance between the composition points and the circular arc length (40151). FIG. 16 shows the determination method. First, a circle is drawn on an x and y plane from the value of ($a_m$, $b_m$, and $r_m$) obtained from the a, b, and r parameter space. The threshold parameter W having a width set by the user (or previously set to the device) is obtained, and a group of points existing in the range becomes the group of points forming the circular arc. The reason why the threshold parameter has the width is that the actual circular arc defect becomes a circular arc having a predetermined width without being overlapped with on one line segment. Next, a distance $r\theta_{gi}$ (i=1, 2 . . . ) between the group of points is obtained, and if the distance is smaller than the threshold parameter $r\theta_{gt}$ of the distance set by the user (or previously set to the device), the group of points is considered to be continuous and if the distance is larger than the threshold parameter $r\theta_{gt}$, it is considered to be separate. Next, the distance $r\theta_{li}$ (i=1, 2 . . . ) (circular arc length) between points of both ends for the group of connected points is obtained, and if the distance is smaller than the threshold parameter $r\theta_{lt}$ of the length set by the user (or previously set to the device), it is considered that the group of points does not have defects and if the distance is larger than the threshold parameter $r\theta_{lt}$, it is considered that the group of points has defects, and the defects are detected. As shown in detail in FIG. 16, if intervals $r\theta_{g1}$ and $r\theta_{g2}$ become $r\theta_{g1} < r\theta_{gt} < r\theta_{g2}$, $r\theta_{11}$ and $r\theta_{12}$ become one circular arc $r\theta_L$, and $r\theta_{13}$ becomes an independent circular arc. Further, if the circular arc $r\theta_L$, $r\theta_{13}$, and $r\theta_{lt}$ become $r\theta_{13} < r\theta_{lt} < r\theta_L$, $r\theta_L$ is finally detected as a defect.

Figure 17A:
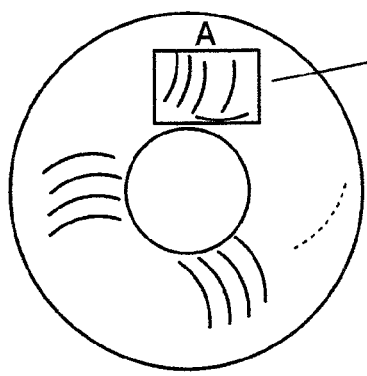
FIG. 17A is a diagram showing an image on a disk surface in a case where several circular arcs determined as the circular arc defects exists in a region A.
Figure 17B:
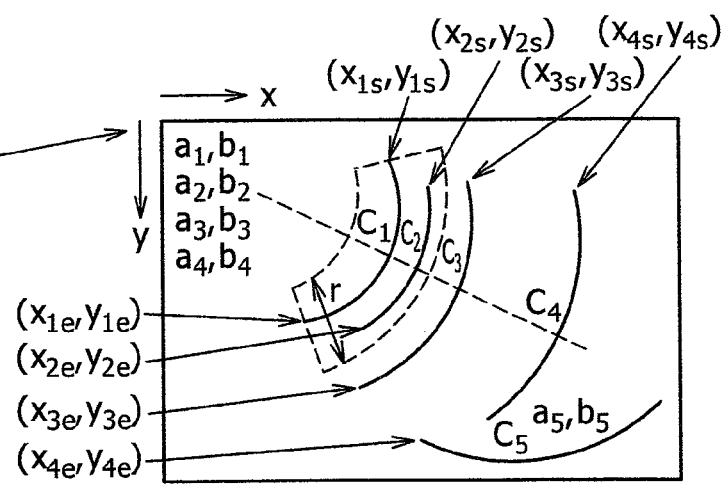
FIG. 17B is an enlarged diagram of the region A.
Figure 20:
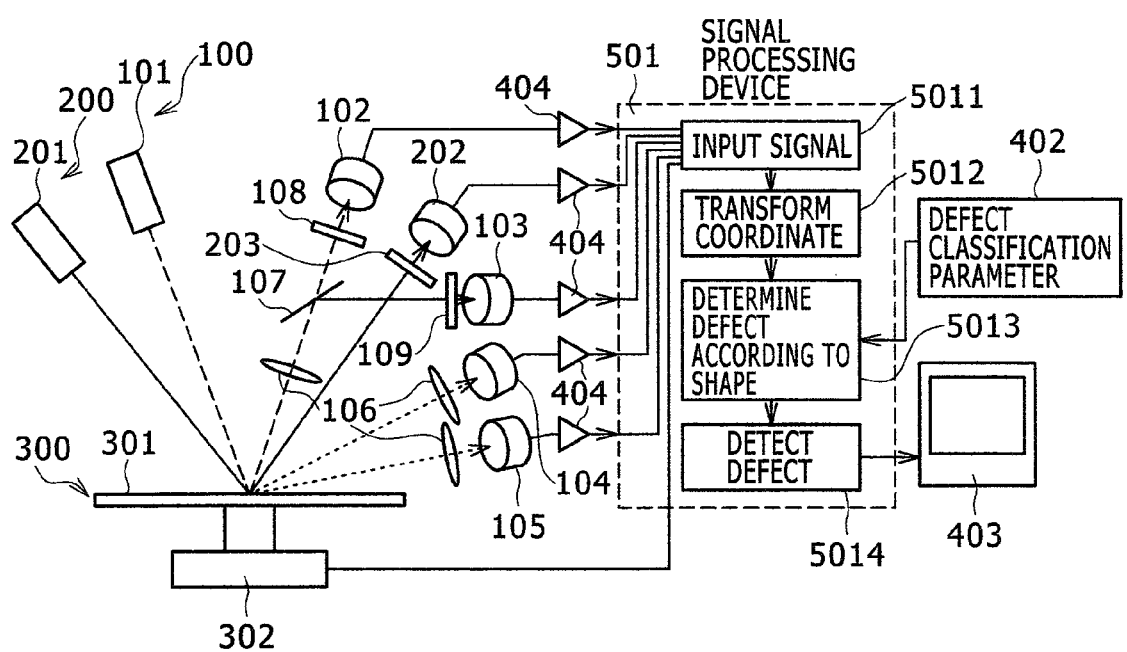
FIG. 20 is a schematic configuration diagram of an apparatus for detecting defects on a disk surface of the related art.

Next, the periodicity determination on the circular arc determined as the circular arc defect is performed (40161). FIGS. 17A and 17B show the determination method. FIG. 17B is an enlarged diagram of a place A portion where several circular arcs determined as the circular arc defect exist in an image on the disk of FIG. 17A. Herein, the determination process on periodicity is performed using the circular arc C1 as a reference of the periodicity determination (40161). First, the same centricity determination is performed by the threshold parameter ($\Delta a$ and $\Delta b$) of the circular arc center coordinate set by the user (or previously set to the device). In other words, with regard to the circular arc coordinate obtained at the time of performing the Hough transformation, the circular arc, which is within the range of $a \pm \Delta a$ and $b \pm \Delta b$, is selected as a candidate line segment having periodicity for the C1. For example, in the case of FIG. 17B, it is determined that ($a_2$ and $b_2$), ($a_3$ and $b_3$) and ($a_4$ and $b_4$) have the same center coordinate, while ($a_5$ and $b_5$) does not have the same center coordinate. Next, a region surrounded in a stripe shape from a starting point coordinate ($x_{ls}$ and $y_{ls}$) an ending point coordinate ($x_{le}$ and $y_{le}$) of C1, and the threshold parameter r of the period set by the user (or previously set to the device) is considered and it is determined that there are the circular arc C1 and the periodicity for the line segment, which is within the region. For example, in the case of FIG. 17B, the region is a region shown by a dotted line and it is determined that C2 included in the region has periodicity. Likewise, if C2 is considered as a reference, it is determined that C3 has periodicity and finally, it is determined that C1, C2, and C3 are the group of circular arcs having periodicity.

Determination on a height for the linear defect subjected to the periodicity determination is finally performed (40171).

Since the convex and concave amount of the disk surface makes the floating amount of the head unstable, it is necessary to perform the defect determination depending on the height. FIGS. 18A to 18E show an example of performing the height determination from the image data. When a surface of a face plate is examined using the optical system shown in FIG. 3, since the height information appears as a contrast on the image, the height determination is performed using the contrast information. In the circular arc determined as the isolative defect and the circular arc having periodicity in the step of the periodicity determination, since a method for determining the height is slightly different, the method that obtains the height for the circular arc determined as the isolative defect will be first described using FIGS. 18A and 18B. With regard to each point from a starting point $P_s$ to an ending point $P_e$ of the circular arc as shown in FIG. 18A, the search region $Q_1$ to $Q_2$ orthogonal to the vertical line to the focused points is set such that the contrast of the line segment is obtained from the concentration value from the point $Q_1$ to the point $Q_2$ in the search region. Describing this through FIG. 18B, it is considered that the search region $Q_1$ to $Q_2$ is divided into three regions $m_1$, $m_2$, and $m_3$ and the circular arc exists in the region $m_2$. Since the contrast is compared with a circumferential portion, an average concentration at the portion is to be computed from portions $m_1$ and $m_3$ that are outside of the circular arc. A difference between the average concentration value and the concentration value of the region $m_2$ is obtained, and the concentration value obtained by integrating the difference in the region $m_2$ is obtained as the contrast at the point $P_n$ in the line segment.

$$C_n = \sum_{i \in D_2} \left| \left\{ \frac{1}{m_1 + m_3} \right\} \cdot \sum_{j \in D_1 + D3} \{f_j\} - f_i \right| \qquad \text{[Equation 9]}$$

If a $C_n$ value is computed from the starting point $P_s$ to the ending point $P_e$ of the circular arc, subjected to the accumulation addition, and divided by the circular arc length $r\theta_L$, the average contrast $C_{av}$ is obtained as follows (Equation 10).

$$C_{av} = \left( \sum_{P_s}^{P_e} C_n \right) / r\theta_L \qquad \text{[Equation 10]}$$

The defect determination can be performed from the contrast of the circular arc defect that is detected by making the correlation between the height measuring value according to the actual profile (measured by other devices) and the obtained contrast value into the shape, as shown in FIG. 18C.

Next, the method for obtaining the height for the circular arc determined as the periodicity defect will be described using FIGS. 18D and 18E. As shown in FIG. 18D, with regard to each point from the starting point $P_s$ to the ending point $P_e$ of the circular arc, the search regions $Q_1$ to $Q_2$ orthogonal to the vertical line to the focused point are set such that the contrast of the line segment is obtained from the concentration value from the point $Q_1$ to the point $Q_2$ in the search region. Describing this through FIG. 18E, since the surface ruggedness continuously occurs in the periodic defect portion, it is considered that the level difference of the concentration continuously occurs. The average concentration value of the search regions $Q_1$ to $Q_2$ is obtained, the absolute value of the difference between the average concentration value and the concentration value of the search regions $Q_1$ to $Q_2$ is obtained, the obtained absolute value of the difference is integrated in the search regions $Q_1$ to $Q_2$, and the value divided by the number of circular arcs included in the regions $Q_1$ to $Q_2$ is obtained as the contrast at the points $P_1$, $P_2$, and $P_3$ in the periodic line segment as follows (Equation 11).

$$C_n = \sum_{i=Q_1}^{Q_2} \left| \sum_{j=Q_1}^{Q_2} \{f_j\} - f_i \right| \qquad \text{[Equation 11]}$$

If the $C_n$ value is computed from the starting point $P_s$ to the ending point $P_e$ of the circular arc, subjected to the accumulation addition, and divided by the circular arc length $r\theta_L$, the average contrast $C_{av}$ is obtained as follows (Equation 12).

$$C_{av} = \left( \sum_{P_s}^{P_e} C_n \right) / r\theta_L \qquad \text{[Equation 12]}$$

The defect determination can be performed from the contrast of the linear defect that is detected by making the correlation between the height measuring value according to the actual profile (measured by other devices) and the obtained contrast value into the shape, as shown in FIG. 18C.

Periodicity circular arc defect detection (40181), isolative circular arc defect detection (40201), and noise detection (40191) are finally formed which are output from the output device 403 by the process. Further, the input of the defect classification parameters (40211) and (40221) is input by the user from the input screen of the defect classification parameter input device 402 as shown in FIG. 19B, and the output of the detection result is displayed by, for example, separate colors for each kind of defect as displayed on the output screen 403.

According to the second embodiment, the periodicity circular arc defect, which is the low aspect defect, can be detected while suppressing false reports and not overlooking the defects regardless of the generation direction of the periodicity circular arc defect.

Third Embodiment

Although the first embodiment relates to the detection of the periodicity linear defect and the second embodiment relates to the detection of the periodicity circular arc defect, it is preferable to simultaneously perform detection of these defects in the same apparatus. In this case, in the flow chart of FIG. 7, it is preferable that after the straight line detection step (4014) and the linear defect determination step (4015) or simultaneously with the above steps, the circular arc detection step (40141) and the circular arc defect determination step (40161) shown in FIG. 14 are performed. Thereby, it is possible to detect the periodicity linear defect and the periodicity circular arc defect, which are the wrinkle defect of the disk.

Fourth Embodiment

Although the above embodiments describe the processing flow for the low aspect defect, the method for detecting defects can be applied to the detection of the linear defect and the circular arc defect, which occur on the disk surface, for example, the detection of the scratch, etc. In this case, the process starts by allowing the light receiving elements 102, 104, and 105 to receive the scattered light from the first light transmitting system 101 of the first optical system and to input the signal to the signal processing device 401. In this case, the defect classification parameter 402 is input by the user according to the kind of detected defects. By this process, it is possible to classify and detect the periodically generated scratch and the isolatively generated scratch.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description and all changes which come within the meaning and range of equivalency of the claims are therefore intended to be embraced therein.

What is claimed is:

1. A method for detecting defects on a disk surface comprising:
    irradiating light on the disk surface;
    detecting linear defects from light reflected on the disk surface;
    determining periodicity on the detected linear defects; and
    classifying and detecting the isolatively generated linear defects and the periodically generated linear defects based on the determination result of the periodicity.

2. The method for detecting defects on a disk surface according to claim 1, wherein the classifying and detecting the isolatively generated linear defects and the periodically generated linear defects performs determination on periodicity for the detected linear defect using a generation coordinate of defect, a generation direction of a line segment, and a period between line segments.

3. A method for detecting defects on a disk surface comprising:
    irradiating light on the disk surface;
    detecting circular arc defects from light reflected on the disk surface;
    determining periodicity on the detected circular arc defects; and
    classifying and detecting the isolatively generated circular arc defects and the periodically generated circular arc defects based on the determination result of the periodicity.

4. The method for detecting defects on a disk surface according to claim 3, wherein the classifying and detecting the isolatively generated circular arc defects and the periodically generated circular arc defects performs determination on the periodicity of the detected circular arc defect using a generation coordinate of the defect, a circular arc center coordinate, and a period between the circular arcs.

5. A method for detecting defects on a disk surface comprising:
    a first step of irradiating a laser beam on the disk surface;
    a second step of forming a disk image from light reflected on the disk surface;
    a third step of performing emphasis on the disk image using a filter passing through only a frequency band where linear defects exist;
    a fourth step of extracting straight components when the defects for the image subjected to the emphasis occur in a linear shape;
    a fifth step of detecting the linear defect by performing a length measuring process on the extracted straight components;
    a sixth step of performing periodicity determination on the detected linear defect; and
    a seventh step of performing height determination when it is determined in the sixth step that there is periodicity;
    wherein, when it is determined in the seventh step that there is a height having a predetermined value or more, it is determined that there is the periodicity linear defect.

6. The method for detecting defects on a disk surface according to claim 5, wherein the first step scans the disk in a spiral shape and the second step performs coordinate transformation on a one-dimensional array signal (polar coordinate) obtained from reflection light to perform the generation of the disk image (rectangular coordinate).

7. The method for detecting defects on a disk surface according to claim 5, wherein the third step exposes the defects for the obtained disk image generated in a radial direction (r direction) and a circumferential direction (θ direction) regardless of directivity by using a two-dimensional frequency filter.

8. The method for detecting defects on a disk surface according to claim 5, wherein the fourth step extracts the straight components from the image whose defects are exposed when the defects occur in a linear shape.

9. The method for detecting defects on a disk surface according to claim 5, wherein the fifth step performs the length measuring process on the extracted straight components using parameters such as a defect width, a defect length, and the like.

10. The method for detecting defects on a disk surface according to claim 5, wherein the sixth step performs the periodicity determination on the detected linear defects using parameters such as a generation direction of defect, an interval between defects, a generation coordinate, and the like.

11. The method for detecting defects on a disk surface according to claim 5, wherein the seventh step determines the height from a contrast of the disk image.

12. A method for detecting defects on a disk surface comprising:
    a first step of irradiating a laser beam on the disk surface;
    a second step of forming a disk image from light reflected on the disk surface;
    a third step of performing emphasis on the disk image using a filter passing through only a frequency band where circular arc defects exist;
    a fourth step of extracting circular arc components when the defects for the image subjected to the emphasis occur in a circular arc shape;
    a fifth step of detecting the circular arc defect by performing a length measuring process on the extracted circular arc components;
    a sixth step of performing periodicity determination on the detected circular arc defect; and
    a seventh step of performing height determination when it is determined in the sixth step that there is the periodicity,
    wherein, when it is determined in the seventh step that there is a height having a predetermined value or more, it is determined that there is the periodicity circular arc defect.

13. The method for detecting defects on a disk surface according to claim 12, wherein the fourth step extracts the circular arc components from the image whose defects are exposed when the defects occur in a circular arc shape.

14. The method for detecting defects on a disk surface according to claim 12, wherein the fifth step performs the length measuring process on the extracted circular arc components using parameters such as a defect width, a defect length, and the like.

15. The method for detecting defects on a disk surface according to claim 12, wherein the sixth step performs the periodicity determination on the detected circular arc defects using parameters such as a generation direction of defect, an interval between defects, a generation coordinate, and the like.

16. The method for detecting defects on a disk surface according to claim 12, wherein the seventh step determines the height from a contrast of the disk image.

17. An apparatus for detecting defects on a disk surface comprising:
  a projecting unit that irradiates a laser beam on the disk surface to scan the disk surface;
  a light receiving unit that receives reflection light of the laser beam due to defects existing on the disk surface; and
  a signal processing unit that detects defects from an output of the light receiving unit to perform determination for each kind of defect,
  wherein the signal processing unit detects linear defects from the output of the light receiving unit, determines periodicity on the detected linear defects, and classifies and detects the isolatively generated linear defects and the periodically generated linear defects based on the determination result of the periodicity.

18. The apparatus for detecting defects on a disk surface according to claim 17, wherein the signal processing unit detects circular arc defects from the output of the light receiving unit, determines periodicity on the detected circular arc defects, and classifies and detects the isolatively generated circular arc defects and the periodically generated circular arc defects based on the determination result of the periodicity.

19. The apparatus for detecting defects on a disk surface according to claim 17, wherein the signal processing unit performs determination on periodicity for the linear defects detected from the output of the light receiving unit using a generation coordinate of defect, a generation direction of a line segment, and a period between line segments.

20. The apparatus for detecting defects on a disk surface according to claim 17, wherein the signal processing unit performs determination on periodicity for the circular arc defects detected from the output of the light receiving unit using a generation coordinate of defect, a circular arc center coordinate, and a period between circular arcs.

* * * * *